US008053594B2

(12) United States Patent
Leconte et al.

(10) Patent No.: US 8,053,594 B2
(45) Date of Patent: Nov. 8, 2011

(54) PREPARATION OF DIESTERS FROM IMIDE/DINITRILE COMPOUNDS

(75) Inventors: Philippe Leconte, Meyzieu (FR); Philippe Marion, Vernaison (FR); Roland Jacquot, Francheville (FR)

(73) Assignee: Rhodia Operations, Aubervilliers Cedex (FR)

( * ) Notice: Subject to any disclaimer, the term of this patent is extended or adjusted under 35 U.S.C. 154(b) by 224 days.

(21) Appl. No.: 12/374,149

(22) PCT Filed: Jul. 5, 2007

(86) PCT No.: PCT/FR2007/001140
§ 371 (c)(1),
(2), (4) Date: May 26, 2009

(87) PCT Pub. No.: WO2008/009792
PCT Pub. Date: Jan. 24, 2008

(65) Prior Publication Data
US 2009/0326261 A1  Dec. 31, 2009

(30) Foreign Application Priority Data
Jul. 18, 2006  (FR) ..................... 06 06510

(51) Int. Cl.
*C07C 67/00* (2006.01)
*C07C 69/34* (2006.01)
(52) U.S. Cl. ....................... 560/204; 560/190
(58) Field of Classification Search ......... None
See application file for complete search history.

(56) References Cited

U.S. PATENT DOCUMENTS

| 2,548,025 | A |   | 4/1951 | Jones |
| 3,567,749 | A | * | 3/1971 | Neugebauer et al. ........... 560/84 |
| 4,248,739 | A | * | 2/1981 | Vaughan et al. ................ 502/63 |
| 4,408,067 | A |   | 10/1983 | Nakamura et al. |
| 2002/0173433 | A1 |   | 11/2002 | Beatty |

FOREIGN PATENT DOCUMENTS

| DE | 730518 |   | 1/1943 |
| GB | 1397729 | * | 6/1975 |

OTHER PUBLICATIONS

Laeckmann et al., "Synthesis and Biological Evaluation of Aroylguanidines Related to Amiloride as Inhibitors of the Human Platelet $Na^+/H^+$ Exchanger", Bioorganic & Medicinal Chemistry, 2002, pp. 1793-1804, vol. 10, No. 6, United Kingdom.

Xue et al., "Transformation of Amides into Esters by the Use of Chlorotrimethylsilane", Journal of the Chinese Chemical Society, 2004, pp. 359-362, vol. 51, No. 2, Taipei, Taiwan.

* cited by examiner

*Primary Examiner* — Paul A Zucker
(74) *Attorney, Agent, or Firm* — Buchanan Ingersoll & Rooney, P.C.

(57) ABSTRACT

Diester compounds are prepared from imide/dinitrile compounds employing a vapor-phase hydrolysis of dinitrile compounds in the presence of alcohol, more particularly from branched dinitrile compounds, such as methylglutaronitrile or branched dinitrile compounds obtained as by-products in a process for the production of adiponitrile by hydrocyanation of butadiene.

24 Claims, No Drawings

PREPARATION OF DIESTERS FROM IMIDE/DINITRILE COMPOUNDS

CROSS-REFERENCE TO PRIORITY/PCT APPLICATIONS

This application claims priority under 35 U.S.C. §119 of FR 0606510, filed Jul. 18, 2006, and is a continuation/national phase of PCT/FR 2007/001140, filed Jul. 5, 2007 and designating the United States (published in the French language on Jan. 24, 2008, as WO 2008/009792 A1; the title and abstract were also published in English), each hereby expressly incorporated by reference in its entirety and each assigned to the assignee hereof.

The present invention relates to a process for the manufacture of diesters from imide or dinitrile compounds.

It relates more particularly to a process for the manufacture of diester compounds from dinitrile compounds employing a vapour-phase hydrolysis of dinitrile compounds.

It relates even more particularly to a process for the manufacture of diesters from branched dinitrile compounds, such as methylglutaronitrile or branched dinitrile compounds obtained as by-products in the process for the manufacture of adiponitrile by hydrocyanation of butadiene.

Oxygenated solvents based on diesters are increasingly used as a replacement for other hydrocarbon, chlorinated or oxygenated solvents more aggressive to the environment.

This is because diester solvents, such as those sold under the known name of Rhodia Solv RDPE, obtained from a mixture of adipic acid, glutaric acid and succinic acid, exhibit the advantage of having a very favourable toxicological profile and are biodegradable and readily recyclable. Diester compounds obtained from branched compounds and more particularly from a mixture of methylglutaronitrile, ethylsuccinonitrile and adiponitrile have also been proposed in unpublished French patent application No. 0602011.

In this patent, a manufacturing process was described which consists in reacting the dinitrile compounds with an alcohol in the presence of an inorganic acid, followed by hydrolysis. This process is known by the name of the Pinner reaction.

However, an ammonium salt is obtained as by-product in this process.

One of the aims of the present invention is to provide a process for the manufacture of diesters from dinitrile compounds which does not exhibit the disadvantages of the processes of the prior art and which in particular does not generate significant amounts of effluents or by-products possibly harmful to the environment.

To this end, a subject-matter of the invention is a process for the manufacture of diester compounds by reaction between an imide compound of following general formula (I):

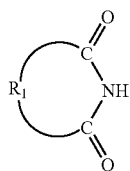

(I)

in which $R_1$ is a linear or branched divalent hydrocarbon radical comprising from 2 to 12 carbon atoms, and an alcohol of following general formula (II):

$$R_2\text{—OH} \quad \text{(II)}$$

in which $R_2$ is a linear or branched, aliphatic, cycloaliphatic, aromatic or arylalkyl hydrocarbon radical comprising from 1 to 20 carbon atoms which can comprise heteroatoms.

According to a preferred embodiment of the invention, the imide compound of formula (I) is obtained by cyclizing hydrolysis of dinitrile compounds of following general formula (III):

$$\text{NC—}R_1\text{—CN} \quad \text{(III)}$$

in which $R_1$ has the meaning indicated above.

This cyclizing hydrolysis reaction is carried out in the vapour phase in the presence of a solid catalyst.

According to a second embodiment of the invention, the process of the invention is carried out in a single stage employing a reaction mixture comprising the dinitrile compound or compounds of formula (III), water and alcohol of formula (II), and a solid catalyst.

In such an embodiment, the cyclizing hydrolysis reaction of the dinitrile compound and the esterification reaction of an imide occur in the reactor.

The reaction medium is brought into contact with the catalyst after having been vaporized.

In this second embodiment, it is advantageous for the amounts of water and alcohol used to make it possible to have a molar ratio R of the number of molecules of alcohol to the number of molecules of water greater by at least 10% than a stoichiometric ratio $R_{stoich}$ of the stoichiometric number of molecules of alcohol for converting the imide formed from the dinitrile to diesters to the stoichiometric number of molecules of water necessary to hydrolyse the dinitrile compound to imide compound.

The stoichiometric number of molecules of water for carrying out the cyclizing hydrolysis of a dinitrile compound is equal to 2.

The stoichiometric number of molecules of alcohol necessary for obtaining the diester is also equal to 2.

Thus, the ratio $R_{stoich}$ is equal to 1.

The ratio R is greater than 1.1 and advantageously less than 20 and preferably less than or equal to 10.

The cyclizing hydrolysis reaction is advantageously carried out at a temperature of less than 500° C., preferably of between 250° C. and 450° C.

Furthermore, the molar ratio of the water to the nitrile compound is between 1 and 10 and preferably between 2 and 5.

The cyclizing hydrolysis reaction carried out in the absence of alcohol (first embodiment) or in the presence of alcohol (second embodiment) is implemented continuously or batchwise in types of reactors which make it possible to use a solid catalyst, either in the form of a fixed bed or in the form of a fluidized bed. The reaction can be carried out at atmospheric pressure or under pressure, for example under a pressure which can range up to 10 bar.

The diester compounds, after condensation, are extracted from the reaction medium by the standard techniques for separating and purifying organic compounds, such as distillation or liquid/liquid extraction, for example.

Likewise, in the first embodiment of the invention, the imide compound obtained by hydrolysis of the dinitrile compound can advantageously be separated from the reaction medium and purified by the standard techniques. However, it is also possible to use the reaction medium obtained after the hydrolysis stage, without separation or purification, directly as reactant in the stage of reaction with an alcohol.

The solid catalyst used by the cyclizing hydrolysis reaction is chosen from the group consisting of metal oxides, such as alumina or titanium oxide, heteropolyacids, zeolites of pentasil and faujasite type, clays, metal phosphates, silica/alumina mixtures and the like.

Thus, the clays suitable for the invention are in particular phyllosilicates, which are categorized by groups according to their nature and their physicochemical properties, among which groups may be mentioned kaolins, serpentines, smectites or montmorillonites, illites or micas, glauconites, chlorites or vermiculites, attapulgites or sepiolites, mixed-layer clays, allophanes or imogolites and high-alumina clays.

Some clays possess a lamellar structure with an expandable network. They exhibit the distinctive feature of adsorbing various solvents, in particular water, between the sheets of which they are composed, which brings about swelling of the solid as a result of the weakening of the electrostatic bonds between the sheets. These clays belong essentially to the smectites group (or also montmorillonite group) and, for some of them, to the vermiculites group.

Their structure is composed of "basic" sheets comprising three layers: two simple layers of $SiO_4$ tetrahedra in which a portion of the silicon can be replaced by other cations in the tetrahedral position, such as $Al^{3+}$ or optionally $Fe^{3+}$, and, between these two layers of tetrahedra, a layer of oxygen octahedra, at the centre of which are situated metal cations, such as $Al^{3+}$, $Fe^{3+}$ or $Mg^{2+}$. This octahedral layer is composed of a compact stack of oxygens originating either from the vertices of the preceding tetrahedra or from hydroxyl groups OH. The compact hexagonal network of these oxygens comprises 6 octahedral cavities.

When the metal cations occupy 4 of these cavities (2 cavities out of 3, as in the case of aluminium, for example), the layer is said to be dioctahedral; when they occupy all the cavities (3 cavities out of 3, as in the case of magnesium, for example), the layer is said to be trioctahedral.

The basic sheets of these clays carry negative charges which are compensated for by the presence of exchangeable cations: alkali metal cations, such as $Li^+$, $Na^+$ or $K^+$, alkaline earth metal cations, such as $Mg^{2+}$ or $Ca^{2+}$, and optionally the hydronium ion $H_3O^+$. The smectites have charge densities on the sheets which are lower than those of the clays of the vermiculite type: approximately 0.66 charge per unit cell, against 1 to 1.4 charges per unit cell for the vermiculites.

The compensating cations are essentially sodium and calcium in the smectites and magnesium and calcium in the vermiculites. From the viewpoint of the charge densities, smectites and vermiculites are intermediates between talc and pyrophyllite, on the one hand, the sheets of which are neutral, and micas, on the other hand, characterized by a high charge density on the sheets (approximately 2 per unit cell) generally compensated for by $K^+$ ions.

The interlayer cations of the smectites and vermiculites can be fairly easily replaced by ion exchange by other cations, such as, for example, ammonium ions or alkaline earth metal ions or rare earth metal ions.

The swelling properties of clays depend on various factors, including the charge density and the nature of the compensating cation.

Thus, smectites, the charge density of which is lower than that of vermiculites, exhibit swelling properties which are markedly superior to those of the latter and thus constitute a highly advantageous category of solids. The repeat distance or basal spacing represents the shortest distance separating two crystallographically identical units situated in two adjacent sheets. The basal spacing of smectites can thus reach, by swelling, values ranging from 1 nm approximately to more than 2 nm.

Mention may be made, among "swelling" phyllite-like silicates of the smectite type, of the following main solids of general formula:

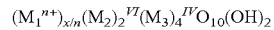

$$(M_1^{n+})_{x/n}(M_2)_2^{VI}(M_3)_4^{IV}O_{10}(OH)_2$$

where
$M_1$ is the interlayer cation
$M_2$ is the metal in the octahedral position
$M_3$ is the metal in the tetrahedral position
x is the number of charges contributed by the cation $M_1$ The dioctahedral smectites
montmorillonite (H, Na, $Ca_{1/2})_x(Mg_xAl_{2-x})^{VI}Si_4^{IV}O_{10}(OH)_2$
beidellite (H, Na, $Ca_{1/2})_xAl_2^{VI}(Al_xSi_{4-x})^{IV}O_{10}(OH)_2$
nontrolite (H, Na, $Ca_{1/2}\ldots)_x(Fe, Al)_2^{VI}(Al_xSi_{4-x})^{IV}O_{10}(OH)_2$ The trioctahedral smectites
hectorite $Na_x(Li_xMg_{3-x})^{VI}Si_4^{IV}O_{10}(OH)_2$
saponite $Na_xMg_3^{VI}(Al_xSi_{4-x})^{IV}O_{10}(OH)_2$
stevensite $Na_{2x}Mg_{3-x}^{VI}Si_4^{IV}O_{10}(OH)_2$ After adsorption in a smectite of water or of a polar organic solvent to saturation, the interlayer spacing (between two sheets) is at a maximum. It can reach a value in the vicinity of 1 nm.

These solids are thus potentially advantageous in catalysis as their potential specific surface and their potential acidity are high.

According to a preferred form of the invention, the clay constituting the cyclisation catalyst of esters or amides of 6-aminocaproïc acid to a lactame is a smectite. More preferably, the clay is montmorillonite.

Some clays unfortunately have the disadvantage of losing their expanded nature on heating to 100° C. and, for this reason, of not retaining the increase in specific surface resulting from their expansion. This is the case in particular with smectites.

Various methods have been described in the prior art for introducing, between the sheets of smectites, pillars or bridges in order to obtain bridged smectites which retain a high interlayer spacing after having been subjected to a heat treatment.

One method, which consists in introducing bridges composed of oligomers of a hydroxide of a metal, in particular of aluminium hydroxide, has been described by Lahav, Shami and Shabtai in Clays and Clay Minerals, vol. 26 (No. 2), pp. 107-115 (1978), and in French Patent 2 394 324. The formation of bridges composed of oligomers of mixed hydroxides of silicon and of boron is described in U.S. Pat. No. 4,248, 739. A technique for bridging smectites by dialysis using hydroxides of aluminium, of chromium, of zirconium and titanium, and the like, is claimed in Patent EP 0 073 718.

The principle of these methods consists in bringing the clay into contact with a solution comprising more or less oligomerized ionic entities of the hydroxy-aluminium type (in the case of aluminium). This operation is generally carried out in a solution of relatively low concentration, at a temperature of less than 80° C. and if possible in the absence of cloudiness formed by the beginning of precipitation of the metal hydroxide. The concentrations of the metal ion and of the clay have to be optimized in order for there to be sufficient formation of solid pillars and for the porosity of the clay not to be greatly reduced by the insertion of an excessively large amount of metal oxide.

When the interlayer alkali metal or alkaline earth metal ions are replaced by protons, either directly, using a very dilute solution, or, preferably, by exchange with an ammonium salt, followed by calcination between 300 and 700° C., the bridged smectites acquire a high acidity, although lower overall than those of conventional zeolites of Y or mordenite type, for example.

According to a specific alternative form of the invention, the catalyst can comprise, in addition to a clay, one or more other metal compounds, often referred to as doping agents, such as, for example, chromium, titanium, molybdenum, tungsten, iron or zinc compounds. Among these doping agents, chromium and/or iron and/or titanium compounds are regarded as the most advantageous. These doping agents usually represent, by weight per weight of clay, from 0% to 10% and preferably from 0% to 5%.

The term "metal compound" is understood to mean both the metal element and the metal ion or any combination comprising the metal element.

Another category of preferred catalyst of the invention consists of a particulate catalyst obtained by shaping at least one simple or mixed inorganic oxide of at least one element chosen from the group consisting of silicon, aluminium, titanium, zirconium, vanadium, niobium, tantalum, tungsten, molybdenum, iron or rare earth metals. These oxides can exist in an amorphous or crystalline form.

According to the invention, the particulate catalyst comprises at least one macroporosity characterized by a pore volume, corresponding to the pores with a diameter of greater than 500 Å, of greater than or equal to 5 ml/100 g.

This macroporosity is advantageously formed during the process of shaping the particles by techniques described below or such as, for example, the addition of a pore-forming agent.

The catalyst can be employed in various forms, such as beads, crushed materials, extrudates in the form of hollow or solid cylindrical granules, a honeycomb or pellets, it being possible for the shaping optionally to be carried out using a binder.

The catalyst may first of all be in the form of beads of inorganic oxides resulting from an oil drop shaping operation (or drop coagulation). Beads of this type can, for example, be prepared by a similar process as that described for the formation of alumina beads in Patents EP-A-0 015 801 or EP-A-0 097 539. The porosity can be controlled in particular, according to the process described in Patent EP-A-0 097 539, by coagulation as drops of an aqueous suspension or dispersion of inorganic oxide.

The beads can also be obtained by the process of agglomeration in a granulator or rotating drum. The catalysts may also be in the form of extrudates of inorganic oxides. The latter can be obtained by kneading and then extruding a material based on the inorganic oxide. The porosity of these extrudates can be controlled by the choice of the oxide employed and by the conditions for preparing this oxide or by the conditions for kneading this oxide before extrusion. The inorganic oxide can thus be mixed, during the kneading, with pore-forming agents. By way of example, the extrudates can be prepared by the process described in U.S. Pat. No. 3,856,708.

Similarly, beads of controlled porosity can be obtained by addition of pore-forming agent and agglomeration in a rotating pan or granulator or by the oil drop process.

According to another characteristic of the invention, the catalyst particles exhibit a specific surface of greater than 10 $m^2/g$ and a pore volume of equal to or greater than 10 ml/100 g, the pore volume corresponding to the pores with a diameter of greater than 500 Å being greater than or equal to 10 ml/100 g.

According to another characteristic of the invention, the catalyst particles exhibit a specific surface of greater than 50 $m^2/g$.

Advantageously, they exhibit a total pore volume of greater than or equal to 15 ml/100 g with a pore volume, corresponding to the pores with a diameter of greater than 200 Å, of greater than or equal to 15 ml/100 g, preferably of greater than or equal to 20 ml/100 g.

These particulate catalysts can also comprise at least one element chosen from the list consisting of silicon, titanium, zirconium, vanadium, niobium, tantalum, tungsten, molybdenum, iron and rare earth metals or can be obtained by deposition and/or adsorption on the support of at least one oxygen compound of at least one element chosen from the group consisting of the elements belonging to Groups 1 to 16 of the Periodic Table of the Elements (new Table), this list also including the rare earth metals. These elements or compounds are deposited or adsorbed on the particulate catalyst.

In the procedure comprising a porous particulate catalyst supporting oxygen compounds of elements, these elements are advantageously chosen from the list consisting of silicon, titanium, zirconium, vanadium, niobium, tantalum, tungsten, molybdenum, phosphorus, boron, iron, alkali metals, alkaline earth metals and rare earth metals. The oxygen compound is advantageously a simple or mixed oxide of one or more of the elements mentioned above.

In this embodiment, the porous catalyst is preferably an aluminium oxide. Advantageously, this alumina exhibits the specific surface and pore distribution characteristics defined above.

The concentration by weight of oxygen compound supported on a porous support is advantageously between 1000 ppm and 30%, expressed as weight of element of the oxygen compound with respect to the total weight of the catalyst. This concentration is more preferably between 0.5% and 15% by weight.

When the porous supports correspond to aluminas in accordance with the invention, the latter are generally obtained by dehydration of gibbsite, bayerite, nordstrandite or their various mixtures. The various processes for the preparation of the aluminas are described in the Kirk-Othmer encyclopaedia, volume 2, pages 291-297.

The aluminas employed in the present process can be prepared by bringing a hydrated alumina, in the finely divided form, into contact with a stream of hot gas at a temperature of between 400° C. and 1000° C., and then maintaining contact between the hydrate and the gases for a period of time ranging from a fraction of a second up to 10 seconds, and finally separating the partially dehydrated alumina and the hot gases. Reference may in particular be made to the process described in U.S. Pat. No. 2,915,365.

It is also possible to autoclave agglomerates of aluminas obtained above, in aqueous medium, optionally in the presence of acid, at a temperature of greater than 100° C. and preferably of between 150° C. and 250° C., for a period of time preferably of between 1 and 20 hours, and then to dry and calcine them.

The calcination temperature is adjusted so that specific surfaces and pore volumes lying within the regions of values indicated above are obtained.

The catalysts of the invention advantageously have a specific surface of greater than 50 $m^2/g$. In addition, they advantageously exhibit pores with a diameter of greater than 0.1 µm, the pore volume contributed by these pores being greater than or equal to 5 ml/100 g, advantageously greater than or equal to 10 ml/100 g.

In a preferred embodiment of the invention, these catalysts also comprise pores with a diameter of equal to or greater than 0.5 μm, the corresponding pore volume being equal to or greater than 5 ml/100 g, preferably greater than or equal to 10 ml/100 g.

This pore volume generated by the pores with a diameter of greater than 500 Å, preferably of greater than 0.1 μm and advantageously of greater than 0.5 μm makes it possible to obtain catalysts with a high cycle time as catalysts for the reaction for the cyclization of esters or amides of 6-aminocaproic acid to give lactams. Thus, such catalysts can be used in industrial processes for the production of lactams.

According to the invention, the catalysts comprising oxygen compounds supported by a porous catalyst are obtained generally by impregnation of the catalyst, in particular of alumina, by a solution of a salt or compounds of the elements mentioned above and are then dried and calcined at a temperature equal to or greater than 400° C. in order to convert, optionally and advantageously, the said compounds or salts to oxygen compounds, preferably to oxides.

The oxides are deposited at the surface of the pores of the porous catalyst.

In another embodiment, the compounds of elements can be added to the material constituting the porous catalyst before it is shaped or during the shaping process.

The impregnated catalysts are preferably calcined under an oxidizing atmosphere, such as air.

According to yet another embodiment of the invention, the catalyst can be a metal phosphate of general formula:

in which:
M represents a divalent, trivalent, tetravalent or pentavalent element chosen from Groups 2a, 3b, 4b, 5b, 6b, 7b, 8, 2b, 3a, 4a and 5a of the Periodic Table of the Elements or a mixture of several of these elements or M=O, Imp represents a basic impregnation compound composed of an alkali metal or alkaline earth metal or of mixtures of several of these metals, in combination with a counteranion in order to provide electrical neutrality, n represents 1, 2 or 3, h represents 0, 1 or 2, p represents a number between 0 and 1/3 and corresponds to a molar ratio of the impregnating material Imp to the impregnated material $(PO_4)_n H_h M$.

Mention may in particular be made, among the metals of Groups 2a, 3b, 4b, 5b, 6b, 7b, 8, 2b, 3a, 4a and 5a of the Periodic Table of the Elements, of beryllium, magnesium, calcium, strontium, barium, aluminium, boron, gallium, indium, yttrium, the lanthanides, such as lanthanum, cerium, praseodymium, neodymium, samarium, europium, gadolinium, terbium, dysprosium, holmium, erbium, thulium, ytterbium and lutetium, zirconium, titanium, vanadium, niobium, iron, germanium, tin or bismuth.

Among the phosphates of lanthanides, it is possible to distinguish a first family which brings together orthophosphates of light rare earth metals, also known as ceric rare earth metals, including lanthanum, cerium, praseodymium, neodymium, samarium and europium. These orthophosphates are dimorphic. They exhibit a hexagonal structure and change towards a monoclinic structure when they are heated at a temperature of 600 to 800° C.

A second family of phosphates of lanthanides brings together the orthophosphates of gadolinium, of terbium and of dysprosium. These orthophosphates exhibit the same structure as the orthophosphates of ceric rare earth metals but additionally exhibit a third crystalline phase of quadratic structure at high temperature (approximately 1700° C.).

A third family of phosphates of lanthanides brings together the orthophosphates of heavy rare earth metals, also known as yttric rare earth metals, including yttrium, holmium, erbium, thulium, ytterbium and lutetium. These compounds crystallize solely in the quadratic form.

Recourse is preferably had, among the various abovementioned families of orthophosphates of rare earth metals, to the orthophosphates of ceric rare earth metals.

Use may be made of metal phosphates of the above formula which are mixtures of phosphates of several of the metals indicated above or mixed phosphates of several of the metals indicated above or also mixed phosphates comprising one or more of the metals indicated above and one or more other metals, such as alkali metals or alkaline earth metals.

The counteranions participating in the formula of the impregnation compound Imp are basic. Use may in particular be made of the hydroxide, phosphate, hydrogenphosphate, dihydrogenphosphate, chloride, fluoride, nitrate, benzoate or oxalate ions, without this list being limiting.

The molar ratio p is preferably between 0.02 and 0.2.

If reference is made to the general techniques for the preparation of phosphates (such as described in particular in Pascal P. "Nouveau traité de chimie minérale" [New Treatise on Inorganic Chemistry], volume X (1956), pages 821-823, and in Gmelins "Handbuch der anorganischen Chemie" [Handbook of Inorganic Chemistry] (8th edition), volume 16 (C), pages 202-206 (1965)), it is possible to distinguish two main routes of access to phosphates. On the one hand, the precipitation of a soluble salt of the metal (chloride, nitrate) by ammonium hydrogenphosphate or phosphoric acid. On the other hand, the dissolution of the oxide or of the carbonate of the metal (which are insoluble) with phosphoric acid, generally under warm conditions, followed by precipitation.

The precipitated phosphates obtained according to one of the routes indicated can be dried, treated with an organic base (such as ammonia) or an inorganic base (such as an alkali metal hydroxide) and be subjected to a calcination, it being possible for these three operations to be carried out in the order shown or in a different order.

The metal phosphates of the above formula for which the symbol p is greater than 0 can be prepared by impregnation of the compound $(PO_4)_n H_n M$, prepared according to one of the techniques described above with a solution or a suspension of Imp in a volatile solvent, such as water, preferably.

The results improve as Imp increases in solubility and the more recently the compound $(PO_4)_n H_n M$ has been manufactured.

Thus, an advantageous process for the preparation of these phosphates consists:

a) in synthesizing the compound $(PO_4)_n H_n M$ and then, preferably without separating $(PO_4)_n H_n M$ from the reaction medium, b) in introducing the impregnating material Imp into the reaction medium;

c) in separating the possible residual liquid from the reaction solid;

d) in drying and optionally calcining.

The performances of these catalysts and in particular their resistance to deactivation can be further improved by calcination. The calcination temperature will advantageously be between 300° C. and 1000° C. and preferably between 400° C. and 900° C. The duration of the calcination may vary within wide limits. By way of indication, it generally lies between 1 hour and 24 hours.

Mention may more particularly be made, among the catalysts preferred in the process of the invention, of lanthanum phosphate, calcined lanthanum phosphate, lanthanum phosphate in combination with a caesium, rubidium or potassium derivative, calcined cerium phosphate, cerium phosphate in combination with a caesium, rubidium or potassium compound, samarium phosphate in combination with a caesium, rubidium or potassium compound, aluminium phosphate, aluminium phosphate in combination with a caesium, rubidium or potassium compound, calcined niobium phosphate, niobium phosphate in combination with a caesium, rubidium or potassium compound, calcined zirconium hydrogenphosphate or zirconium hydrogenphosphate in combination with a caesium, rubidium or potassium compound.

The orthophosphates described above can be used as a mixture with phosphoric acid ($H_3PO_4$).

Use may also be made, as catalyst, of pyrophosphates of rare earth metals, in particular of lanthanum, alone or as a mixture with the orthophosphates described above. Such catalysts are described in European Patent EP1066255.

The preferred dinitrile compounds of the invention are compounds obtained by hydrocyanation of butadiene and more particularly still the branched dinitrile compounds produced by the double hydrocyanation of butadiene, such as methylglutaronitrile or ethylsuccinonitrile.

Advantageously, the process of the invention uses a mixture of dinitrile compounds comprising methylglutaronitrile, ethylsuccinonitrile and adiponitrile.

This mixture is obtained in particular by separation, for example by distillation, from the reaction medium obtained after hydrocyanation of the pentenenitriles, in the process for the production of adiponitrile by double hydrocyanation of butadiene.

The alcohols suitable for the invention are, for example, branched or unbranched and cyclic or acyclic aliphatic alcohols which can comprise an aromatic nucleus and which can comprise from 1 to 20 carbon atoms. Mention may be made, as preferred examples, of the following alcohols: methanol, propanol, isopropanol, benzyl alcohol, ethanol, n-butanol, isobutanol, pentanols, cyclohexanol, hexanol, isooctanol or 2-ethylhexanol.

The composition or the diesters obtained by the process of the invention can be used alone or as a mixture with other solvents or with water in the solution or emulsion form. In particular, they can be used as a mixture with the diesters of the linear diacids cited above (RPDE).

These diester compounds have applications as solvent in numerous fields, such as paints, varnishes and lacquers, the industry for coating surfaces or any other article, such as cables, for example, the ink industry, lubricants for textiles, binders and resins for foundry cores and moulds, cleaning products, cosmetic formulations, for the implementation of certain chemical reactions, in soil and plant treatment compositions and more generally the use, alone or in a formulation, as cleaning, pickling or degreasing solvent in any industrial or domestic activity.

These diester compounds can also be used as plasticizers for some plastics or as monomers for the manufacture of polymers.

Other advantages or characteristics of the invention will be described in more detail and will be better illustrated in the light of the examples given below purely by way of illustration.

Synthesis of the Diesters in One Stage

A medium comprising water, methanol and a mixture of dinitrile compounds with the following composition by weight:

86% by weight of methylglutaronitrile
11% by weight of ethylsuccinonitrile
3% by weight of adiponitrile is introduced using a syringe driver, at a flow rate of 1 ml/h, into a Pyrex tube placed vertically in an oven, the temperature of which is 300° C., and swept by a 1 l/h nitrogen stream. 4 ml of catalyst are placed between 2 layers of glass powder with a volume of 5 ml. Injection is carried out immediately above the upper layer of glass and the nitrogen stream carries the products through the catalyst bed. At the outlet of the oven, the gases are condensed in a tube placed in an ice bath and are then analysed by gas chromatography.

The medium introduced has the following molar composition:

1 mol of dinitrile compounds
2 mol of water
8 mol of methanol

A test was carried out using, as catalyst, macroporous alumina sold by Procatalyse under the name SCM 139 XL. The degree of conversion of the dinitrile compounds is 25%. The yield of diesters is 0.3%. It was found that the reaction medium comprises cyanoesters, corresponding to an intermediate product capable of being converted to diesters. The yield of cyanoesters is 2.4%.

A second test was carried out using, as catalyst, a mixture of 2 mol of lanthanum orthophosphate and one mole of orthophosphoric acid. The degree of conversion of the dinitrile compounds is 62%. The yield of diesters is 3%. It was found that the reaction medium comprises cyanoesters, corresponding to an intermediate product capable of being converted to diesters. The yield of cyanoesters is 2%.

A third test was carried out using, as catalyst, (anatase) titanium oxide. The conversion of the dinitrile compounds is 78%. The yield of diesters is 3%. The reaction medium additionally comprises 15% of cyanoesters and 20% of a mixture of imides.

Synthesis of the Diesters in 2 Stages

EXAMPLE 3

1 ml/h of a mixture of dinitriles and 1 ml/h of water are coinjected, using 2 syringe drivers, over a catalytic fixed bed, composed of 4 ml of (anatase) titanium oxide placed between 2 layers of 5 ml of glass powder, heated to 275° C. and swept by a 3 l/h nitrogen stream. At the outlet of the reactor, the gases are condensed in a receiver placed in an ice bath. After reacting for 6 h, the products obtained are analysed by gas chromatography. For a conversion of the dinitriles of 97%, a yield of mixed imides of 94% is then obtained.

EXAMPLE 4

1 g of a mixture of imides and 10 ml of methanol are introduced into a reactor and 0.2 g of anatase titanium oxide is added. The reaction mixture is heated under autogenous pressure at 250° C. for 5 hours. After cooling and filtering off the catalyst, the medium is analysed by gas chromatography. For a conversion of imides of 90%, the yield of dimethyl esters is 60%.

EXAMPLE 5

1 g of a mixture of imides and 10 ml of 1-propanol are introduced into a reactor and 0.2 g of anatase titanium oxide is added. The reaction mixture is heated at 250° C. under autogenous pressure for 5 hours. After cooling and filtering off the catalyst, the reaction medium is analysed by gas chromatography. For a conversion of imides of 55%, a yield of dipropyl esters of 40% is obtained.

EXAMPLE 6

1 g of a mixture of imides and 10 ml of 1-butanol are introduced into a reactor and 0.2 g of anatase titanium oxide is added. The reaction mixture is heated at 250° C. under autogenous pressure for 5 hours. After cooling and filtering off the catalyst, the reaction medium is analysed by gas chromatography. For a conversion of imides of 50%, a yield of dibutyl esters of 38% is obtained.

EXAMPLE 7

1 g of a mixture of imides and 10 ml of isobutyl alcohol are introduced into a reactor and 0.2 g of anatase titanium oxide is added. The reaction mixture is heated at 250° C. under autogenous pressure for 5 hours. After cooling and filtering off the catalyst, the reaction medium is analysed by gas chromatography. For a conversion of imides of 52%, a yield of diisobutyl esters of 40% is obtained.

EXAMPLE 8

In the Gas Phase

A solution composed of 1 g of a mixture of imides in solution in 8 ml of methanol is injected at a flow rate of 5 ml/h over a catalytic bed, composed of 4 ml of (anatase) titanium oxide placed between 2 layers of 5 ml of glass powder, heated to 275° C. and swept by a 3 l/h nitrogen stream. At the outlet of the reactor, the gases are condensed in a receiver placed in an ice bath. After reacting for 6 hours, the products obtained are analysed by GC. For a conversion of imides of 62%, a yield of dimethyl esters of 30% is obtained.

EXAMPLE 9

A solution composed of 1 g of a mixture of imides in solution in 8 ml of 1-pentanol is injected at a flow rate of 5 ml/h over a catalytic bed, composed of 4 ml of (anatase) titanium oxide placed between 2 layers of 5 ml of glass powder, heated to 275° C. and swept by a 3 l/h nitrogen stream. At the outlet of the reactor, the gases are condensed in a receiver placed in an ice bath. After reacting for 6 hours, the products obtained are analysed by GC. For a conversion of imides of 70%, a yield of dipentyl esters of 45% is obtained.

The invention claimed is:
1. A process for the preparation of a diester compound the method comprising:
  (a) forming an imide compound having the formula (I):

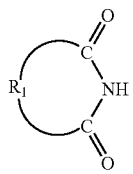

(I)

by hydrolysis of a dinitrile compound having the formula (III):

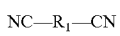

(III)

wherein the hydrolysis of the dinitrile compound is carried out in the vapor phase in the presence of a solid catalyst,
in which $R_1$ is a linear or branched divalent hydrocarbon radical having from 2 to 12 carbon atoms, and
  (b) reacting the imide compound with an alcohol having the following general formula (II):

(II)

in which $R_2$ is a linear or branched, aliphatic, cycloaliphatic, aromatic or arylalkyl hydrocarbon radical having from 1 to 20 carbon atoms and which can contain heteroatom(s).

2. The process as defined by claim 1, wherein the hydrolysis of the dinitrile compound of formula (III) and the reaction between the alcohol and the imide are carried out simultaneously in a single reactor.

3. The process as defined by claim 1, wherein the amount of alcohol ROH and of water employed are determined to provide a molar ratio R of the number of molecules of alcohol to the number of molecules of water greater by at least 10% than a stoichiometric ratio $R_{stoich}$ of the stoichiometric number of molecules of alcohol for converting the imide formed from the dinitrile to diesters to the stoichiometric number of molecules of water necessary to hydrolyze the dinitrile compound to imide compound.

4. The process as defined by claim 3, wherein the ratio R is greater than 1.1.

5. The process as defined by claim 1, wherein the dinitrile compounds are selected from the group consisting of methylglutaronitrile, ethylsuccinonitrile, adiponitrile and their mixtures.

6. The process as defined by claim 1, wherein the alcohol is selected from the group consisting of methanol, propanol, isopropanol, benzyl alcohol, ethanol, n-butanol, isobutanol, pentanols, cyclohexanol, hexanol, isooctanol, 2-ethylhexanol and mixtures thereof.

7. The process as defined by claim 1, wherein the hydrolysis reaction is carried out at a temperature of less than 500° C.

8. The process as defined by claim 1, wherein the molar ratio of the water to the nitrile compound ranges from 1 to 10.

9. The process as defined by claim 1, wherein the solid catalyst is selected from among a metal oxide, alumina, a heteropolyacid, zeolite, pentasil, faujasite, a clay, a metal phosphate, titanium oxide, a silica/alumina mixture.

10. The process as defined by claim 9, wherein the solid catalyst is a clay selected from among the kaolins, serpentines, smectites, montmorillonites, illites, micas, glauconites, chlorites, vermiculites, attapulgites, sepiolites, mixed-layer clays, allophanes, imogolites and high-alumina clays.

11. The process as defined by claim 10, wherein the clay is a montmorillonite.

12. The process as defined by claim 10, wherein the clay is bridged.

13. The process as defined by claim 9, wherein the catalyst is a particulate catalyst obtained by shaping at least one simple or mixed inorganic oxide of at least one element selected from the group consisting of silicon, aluminum, titanium, zirconium, vanadium, niobium, tantalum, tungsten, molybdenum, iron and rare earth metals and which comprises at least one macroporosity characterized by a pore volume, corresponding to the pores with a diameter of greater than 500 Å, of greater than or equal to 5 ml/100 g.

14. The process as defined by claim 13, wherein the particulate catalyst exhibits a specific surface of greater than 10 m²/g and a total pore volume of greater than or equal to 10 ml/100 g, the pore volume corresponding to the pores having a diameter of greater than 500 Å being greater than or equal to 10 ml/100 g.

15. The process as defined by claim 13, wherein the catalyst exhibits a specific surface of greater than 50 m²/g.

16. The process as defined by claim 13, wherein the catalyst exhibits a total pore volume of greater than or equal to 20 ml/100 g with a pore volume, corresponding to the pores having a diameter of greater than 70 Å, of greater than or equal to 20 ml/100 g.

17. The process as defined by claim 13, wherein the particulate catalyst comprises an aluminum oxide.

18. The process as defined by claim 13, wherein the particulate catalyst comprises at least one element selected from the group consisting of silicon, titanium, zirconium, vanadium, niobium, tantalum, tungsten, molybdenum, iron and rare earth metals or at least one oxygen compound of at least one element selected from the group consisting of the elements of Groups 1 to 16 of the Periodic Table of Elements, and also including the rare earth metals, deposited or adsorbed on the particulate catalyst formed of simple or mixed inorganic oxides.

19. The process as defined by claim 1, wherein the catalyst is a metal phosphate having the formula:

$$(PO_4)_n H_h M, (Imp)_p$$

in which:
  M is a divalent, trivalent, tetravalent or pentavalent element selected from Groups 2a, 3b, 4b, 5b, 6b, 7b, 8, 2b, 3a, 4a and 5a of the Periodic Table of Elements or a mixture thereof or M=O,
  Imp is a basic impregnation compound comprising an alkali metal or alkaline earth metal or mixture thereof, in combination with a counteranion to provide electrical neutrality,
  n is 1, 2 or 3,
  h is 0, 1 or 2,
  p is a number ranging from 0 to 1/3 and which corresponds to a molar ratio of the impregnating material Imp to the impregnated material (PO4)nHhM.

20. The process as defined by claim 1, wherein the catalyst comprises a pyrophosphate of a rare earth metal.

21. The process as defined by claim 20, wherein the catalyst comprises a mixture of pyrophosphates of rare earth metals and of orthophosphates of rare earth metals.

22. The process as defined by claim 20, wherein the catalyst comprises a mixture of orthophosphates of rare earth metals and of phosphoric acid.

23. The process as defined by claim 1, wherein the yield of the diesters is greater than that produced by a one-step process.

24. The process as defined by claim 1, wherein the yield of the diester is at least 30%.

* * * * *